United States Patent
Dickerhoff

[19]

[11] Patent Number: 6,112,348
[45] Date of Patent: Sep. 5, 2000

[54] INFLATABLE BLANKET HAVING OPENINGS FORMED THEREIN

[75] Inventor: Scott D. Dickerhoff, Ballwin, Mo.

[73] Assignee: Mallinckrodt Inc., St. Louis, Mo.

[21] Appl. No.: 09/233,088

[22] Filed: Jan. 19, 1999

Related U.S. Application Data

[63] Continuation of application No. 08/708,904, Sep. 5, 1996, Pat. No. 5,890,243, which is a continuation of application No. 08/344,425, Nov. 23, 1994, abandoned.

[51] Int. Cl.$^7$ .................................................. A47C 27/08
[52] U.S. Cl. ..................................................... 5/482; 5/941
[58] Field of Search ............................ 5/421, 423, 941, 5/726, 482, 461, 467, 485, 486, 494; 128/847; 607/104, 107, 83, 105, 106, 108, 114

[56] References Cited

U.S. PATENT DOCUMENTS

| | | |
|---|---|---|
| 630,565 | 8/1899 | Safran . |
| 721,250 | 2/1903 | Strom . |
| 1,291,191 | 1/1919 | Semple . |
| 1,590,522 | 6/1926 | Kalman . |
| 1,777,982 | 10/1930 | Popp . |
| 2,093,834 | 9/1937 | Gaugler . |
| 2,110,022 | 3/1938 | Kliesrath . |
| 2,122,964 | 7/1938 | Sweetland . |
| 2,235,966 | 3/1941 | Summers . |
| 2,512,559 | 6/1950 | Williams . |
| 2,601,189 | 6/1952 | Wales, Jr. . |
| 2,617,915 | 11/1952 | Blair . |
| 2,700,165 | 1/1955 | Talisman . |
| 2,706,988 | 4/1955 | Weber .................................. 128/402 |
| 2,722,694 | 11/1955 | Bryant . |
| 2,791,168 | 5/1957 | Mauch . |
| 2,834,033 | 5/1958 | O'Brien . |
| 2,998,817 | 9/1961 | Armstrong . |
| 3,034,132 | 5/1962 | Landsberger . |
| 3,307,554 | 3/1967 | Thornton et al. . |
| 3,308,850 | 3/1967 | Gill . |
| 3,610,251 | 10/1971 | Sanderson . |
| 3,674,034 | 7/1972 | Hardy . |
| 3,738,367 | 6/1973 | Hardy . |
| 3,740,777 | 6/1973 | Dee . |
| 3,757,366 | 9/1973 | Sacher . |
| 3,844,339 | 10/1974 | Kranz . |
| 4,026,299 | 5/1977 | Sauder . |
| 4,094,357 | 6/1978 | Sgroi . |
| 4,398,535 | 8/1983 | Guibert . |
| 4,457,295 | 7/1984 | Roehr . |
| 4,572,188 | 2/1986 | Augustine et al. . |
| 4,574,796 | 3/1986 | Lundström et al. . |
| 4,653,131 | 3/1987 | Diehl . |
| 4,660,388 | 4/1987 | Greene, Jr. . |
| 4,777,802 | 10/1988 | Feher . |
| 4,807,644 | 2/1989 | Sandhaus . |
| 4,853,996 | 8/1989 | Harrigan et al. . |
| 4,867,230 | 9/1989 | Voss . |
| 4,959,877 | 10/1990 | Covil . |
| 4,997,230 | 3/1991 | Spitalnick . |
| 5,022,110 | 6/1991 | Stroh . |
| 5,044,364 | 9/1991 | Crowther . |

(List continued on next page.)

FOREIGN PATENT DOCUMENTS

| | | |
|---|---|---|
| 1325484 | 12/1993 | Canada . |
| 0311336 | 4/1989 | European Pat. Off. . |
| 149244 | 8/1931 | Switzerland . |
| 8503216 | 8/1985 | WIPO . |
| 9403131 | 2/1994 | WIPO . |
| 9520371 | 8/1995 | WIPO . |
| 9535077 | 12/1995 | WIPO . |
| 9603098 | 2/1996 | WIPO . |

*Primary Examiner*—Terry Lee Melius
*Assistant Examiner*—Fredrick Conley
*Attorney, Agent, or Firm*—Rothwell, Figg, Ernst & Manbeck, P.C.

[57] ABSTRACT

The present invention relates to a blanket for use with forced air convection systems, wherein the blanket includes openings through which a patient's toes or feet may protrude, the openings being located near the air inlet port of the blanket. By providing a blanket with such openings, comfort for the patient can be increased and slippage of the blanket can be reduced.

7 Claims, 9 Drawing Sheets

U.S. PATENT DOCUMENTS

| | | |
|---|---|---|
| 5,097,548 | 3/1992 | Heck et al. . |
| 5,106,373 | 4/1992 | Augustine et al. . |
| 5,125,238 | 6/1992 | Ragan et al. . |
| 5,165,400 | 11/1992 | Berke . |
| 5,184,612 | 2/1993 | Augustine . |
| 5,265,599 | 11/1993 | Stephenson . |
| 5,269,369 | 12/1993 | Faghri . |
| 5,277,695 | 1/1994 | Johnson, Jr. . |
| 5,300,098 | 4/1994 | Philipot . |
| 5,300,100 | 4/1994 | Hickle et al. . |
| 5,300,101 | 4/1994 | Augustine et al. . |
| 5,300,102 | 4/1994 | Augustine et al. . |
| 5,304,213 | 4/1994 | Berke et al. . |
| 5,304,217 | 4/1994 | Stephenson . |
| 5,318,568 | 6/1994 | Kaufmann et al. . |
| 5,324,320 | 6/1994 | Augustine et al. . |
| 5,336,250 | 8/1994 | Augustine . |
| 5,343,579 | 9/1994 | Dickerhoff et al. . |
| 5,350,417 | 9/1994 | Augustine . |
| 5,360,439 | 11/1994 | Dickerhoff et al. . |
| 5,384,924 | 1/1995 | Dickerhoff et al. . |
| 5,392,847 | 2/1995 | Stephenson . |
| 5,405,370 | 4/1995 | Irani . |
| 5,405,371 | 4/1995 | Augustine et al. . |
| 5,408,712 | 4/1995 | Brun . |
| 5,433,083 | 7/1995 | Kuramarohit . |
| 5,443,488 | 8/1995 | Namenye et al. . |

INFLATABLE BLANKET HAVING OPENINGS FORMED THEREIN

The present application is a continuation of U.S. Ser. No. 08/708,904, filed Sep. 5, 1996, now U.S. Pat. No. 5,890,243 allowed, which is a continuation of U.S. Ser. No. 08/344,425, filed Nov. 23, 1994, abandoned.

BACKGROUND

Hypothermia is a condition of subnormal body temperature and presents serious consequences to the patient suffering therefrom. It has been shown that nearly seventy five percent of all patients who undergo surgical procedures develop hypothermia. This equates to approximately fourteen million patients a year in the United States alone. The hypothermic condition is brought on by many factors including anesthesia, the air conditioning of the operating room, and the infusion of cold blood, I-V solutions, or irrigating fluids.

Several methods and products have been developed to help prevent hypothermia from occurring; such as the use of infrared lamps, cotton blankets, and warm water mattresses. However, none of these methods and products have proven completely successful. In fact, it has been shown that these methods and products can not even prevent the patients from losing their endogenous heat. (See Journal of Post Anesthesia Nursing, Vol. 5, No. 4, August 1990, pp 254–263).

Another method of helping to prevent hypothermia that has proven very effective is the use of forced warm air convection. As early as 1937, a refrigeration blanket using cold air convection was suggested in U.S. Pat. No. 2,093,834 to Gaugler. This blanket included a plurality of layers for channeling airflow from an inlet port. Non-inflatable portions were provided around the periphery of the blanket to secure the blanket around the body. Gaugler does not mention hypothermia treatment and does not suggest that the blanket could be used to supply warm air.

U.S. Pat. No. 2,512,559 to Williams also relates to a blanket for providing cooled air to a person. The blanket in Williams comprised a plurality of thin sheets of material connected together at a plurality of discrete locations and connected together in a continuous line about the peripheral edge. An air inlet was provided to communicate with space between the sheets to allow cool air to be supplied thereto. Again, no mention of hypothermia treatment or the supply of warm air is made.

In U.S. Pat. No. 4,572,188 to Augustine, et al., a forced air convection system which can supply either cool or warm air to a blanket is described. The blanket in Augustine, et al. comprises a plurality of inflatable hollow tubes having their interiors connected together through transverse openings. An entry port is provided in the upper surface of the blanket for admitting the cool or warm air and small exit ports are provided through the lower surface to allow the cool or warm air to flow out toward a body covered by the blanket.

Other patents relating to the supply of cool or warm air to a person through an inflatable blanket include U.S. Pat. No. 4,660,388 to Greene, Jr.; U.S. Pat. No. 4,777,802 to Feher; and U.S. Pat. No. 4,867,230 to Voss. Each of these patents describe blankets having various attributes and configurations to supply cool or warm air to the person.

While there are a number of patents noted above and others not mentioned which relate to inflatable blankets for use in supplying cool or warm air to a patient, there remains a need in the art for improvements to forced air convection systems.

OBJECTS OF THE INVENTION

It is one object of the present invention to provide a blanket for a forced air convection system that is more comfortable for the patient when in use.

It is another object of the present invention to provide a blanket for a forced air convection system which remains in place on the patient more consistently.

SUMMARY OF THE INVENTION

The above objects and others are accomplished according to the present invention by providing a blanket having openings through which the patent's feet may protrude when the blanket is in use.

DETAILED DESCRIPTION OF THE INVENTION

Figure 1:
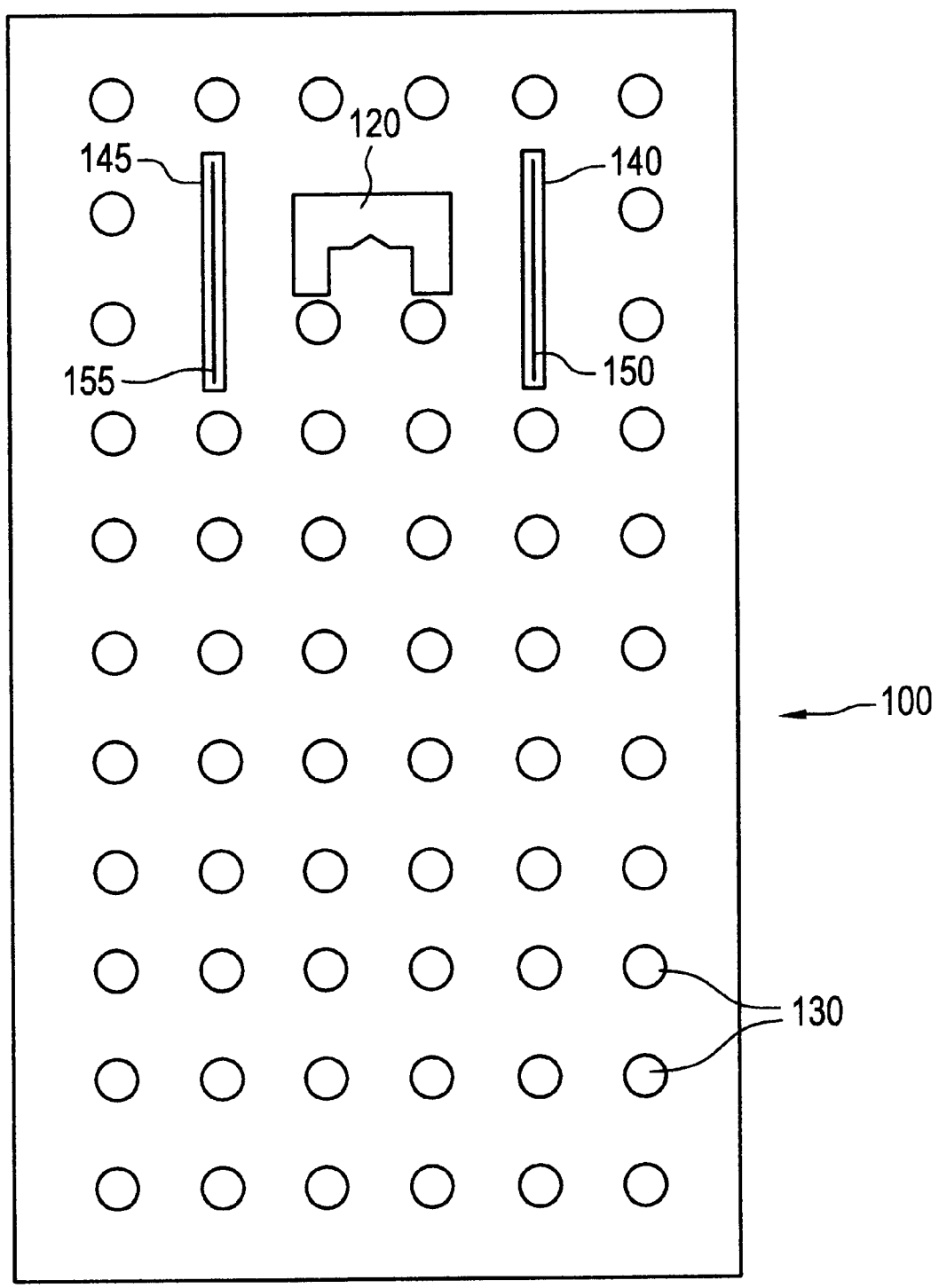
FIG. 1 is a plan view of a blanket for a forced air convection system according to one embodiment of the present invention.

FIG. 1 is a plan view of a blanket, generally designated by reference numeral 100, for a forced air convection system. The blanket, 100, has a generally rectangular shape and includes an inlet port 120. The blanket 100, may be of any standard design known in the prior art, but preferably comprises two sheets of material which are sealed together along their peripheral edges and are connected together at connection spot welds 130, discretely located on the interior surface portions of the sheets. By connecting the sheets of the blanket 100, in this manner, the blanket 100, may be inflated by supplying air to the interior area formed between the sheets of material.

The inlet port 120, communicates with the interior of the blanket 100, and may be used to supply air to the interior of the blanket 100, so as to inflate blanket 100. The lower sheet of the blanket 100, may be provided with a plurality of small exit ports to allow air to escape from the blanket 100, toward a patient.

In use, the blanket 100, may be placed over the body of a patient so that the inlet port 120, is located between the legs of the patient in the vicinity of the patient's knees. With the inlet port 120, located in such a position the hose required for connection to an air supply will necessarily be located between the legs of the patient and will run from the connection with the inlet port 120, toward the patient's feet and beyond to the end of the operating table. This can be disadvantageous because the hose pulls the blanket down around the patient's legs and feet, which can cause significant discomfort to the patient. The greatest discomfort is in the area of the toes and feet of the patient which are often constrained and stressed by the pressure of the blanket and air hose.

A further general disadvantage of blankets for forced air systems arises because of the tendency of the blankets to slide about on the patient. This is especially true when the blankets are used to warm patients in a post anesthesia care unit (PACU) following surgery, when patients are reviving from anesthesia and tend to move about. Such movements can cause a blanket to slide off of the patient and may result in uneven warming to the patient.

To overcome the disadvantages noted above, the blankets according to the present invention are provided with openings through which the patient's toes and feet can protrude.

In particular, as shown in FIG. 1, a pair of openings 140, 145, are provided. In the configuration shown in FIG. 1, the openings 140, 145 are formed in the shape of slits which run lengthwise with the blanket 100, but it will be recognized that almost any configuration which allows the patient's feet to protrude through the openings 140, 145, can be used.

In one embodiment of the present invention, the openings are permanently open. In this embodiment the openings are formed simply by sealing the two sheets of the blanket together around the peripheral edges of the openings. However, when the openings are permanently open warm air may constantly escape from below the blanket which may be undesirable in certain instances.

Therefore, in accordance with another embodiment of the present invention, as shown in FIG. 1, the openings 140, 145, are provided with perforations 150, 155, respectively. These perforations 150, 155 prevent the escape of warming air from the blanket 100, until such time as the perforations 150, 155 are opened.

As noted above, the openings may be formed in almost any configuration which allows the patient's toes or feet to protrude therethrough. In particular, the openings may be slits which run lengthwise to the blanket, widthwise to the blanket, diagonally to the blanket or be composed of a combination of lengthwise and widthwise portions. Further, the openings may be circular, oval or rectangular in shape. Other geometric shapes are equally applicable to the present invention. When the openings are in the form of such a geometric shape, they may be initially open or may be initially closed by a perforated section which can be cutout or punched out by the user.

Figure 3A:
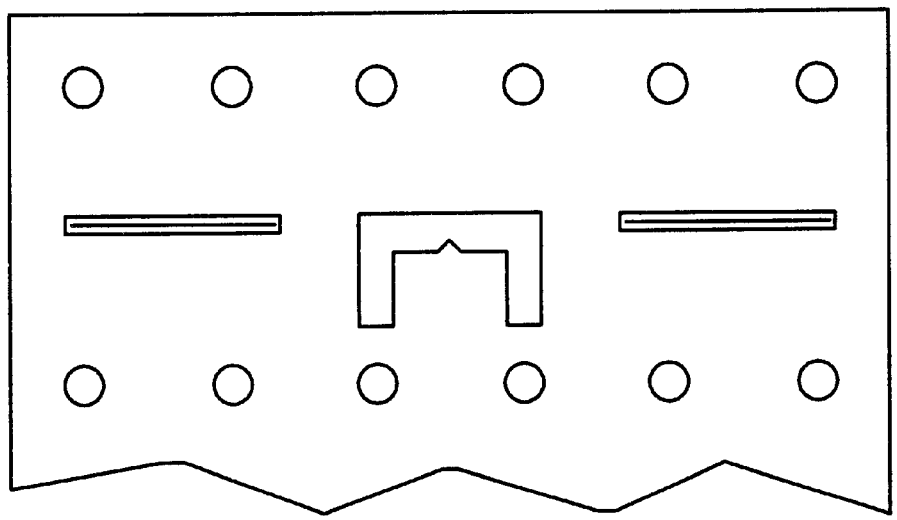
FIGS. 3A through 3L are plan views of the lower portion of a blanket according to the present invention showing different configurations of openings.
Figure 3B:
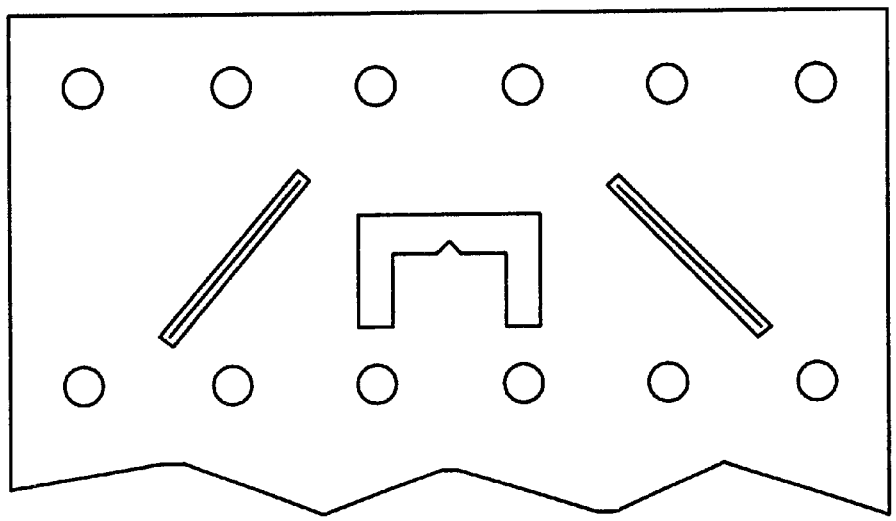
Figure 3C:
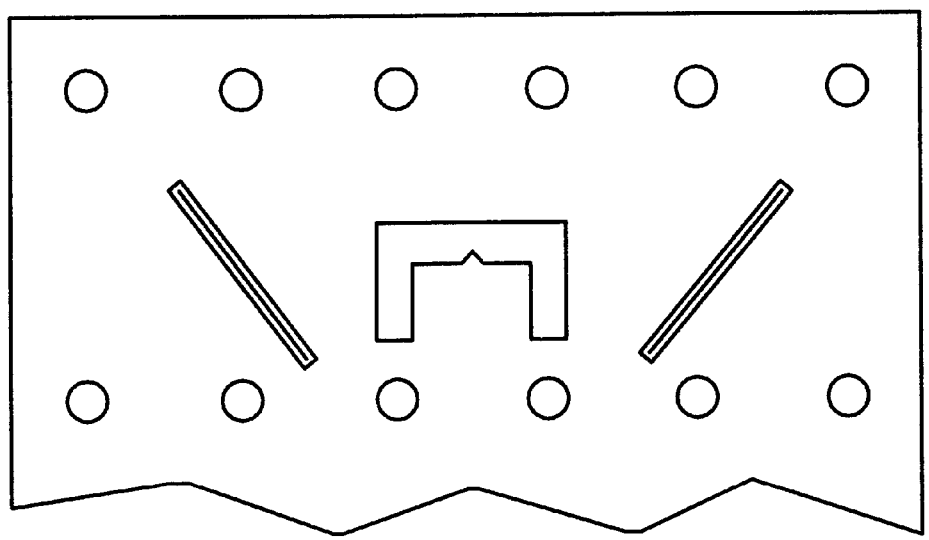
Figure 3D:
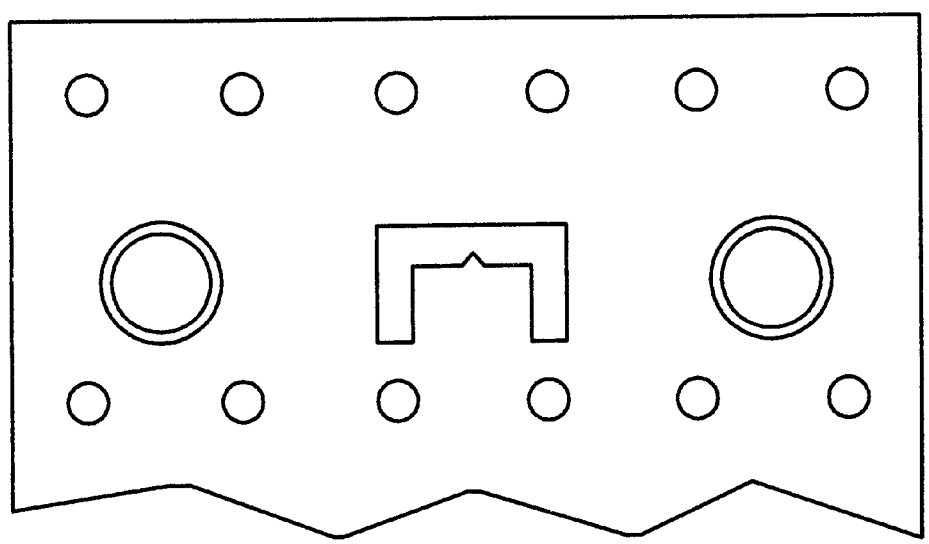
Figure 3E:
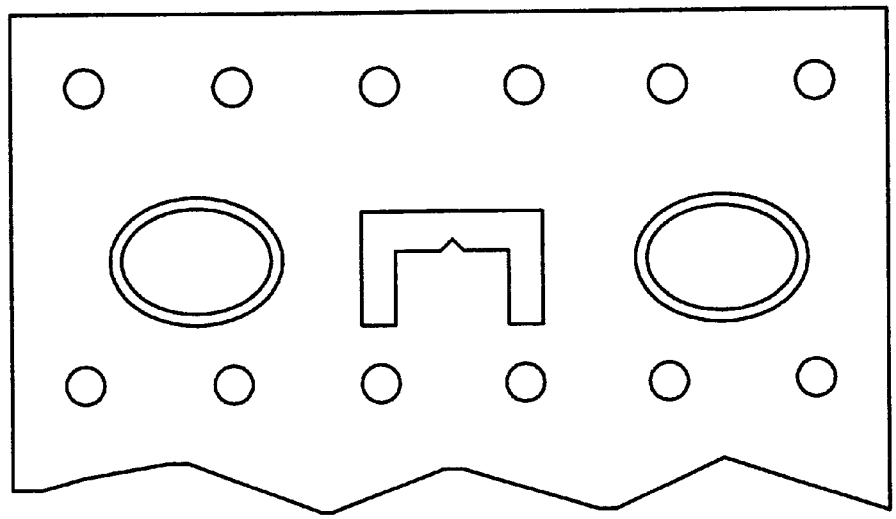
Figure 3F:
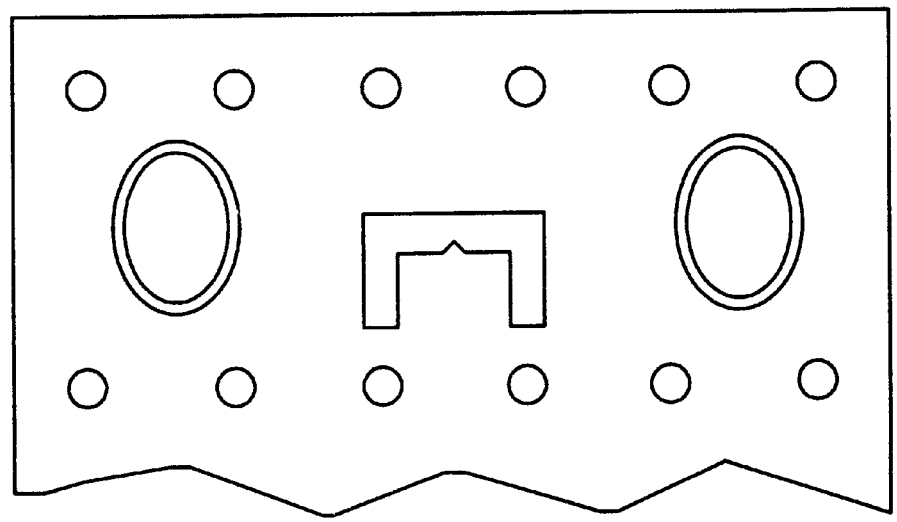
Figure 3G:
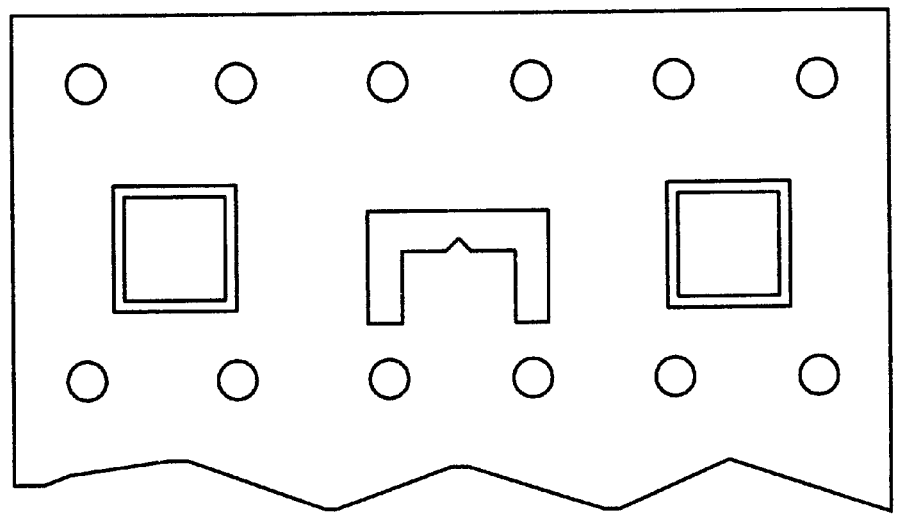
Figure 3H:
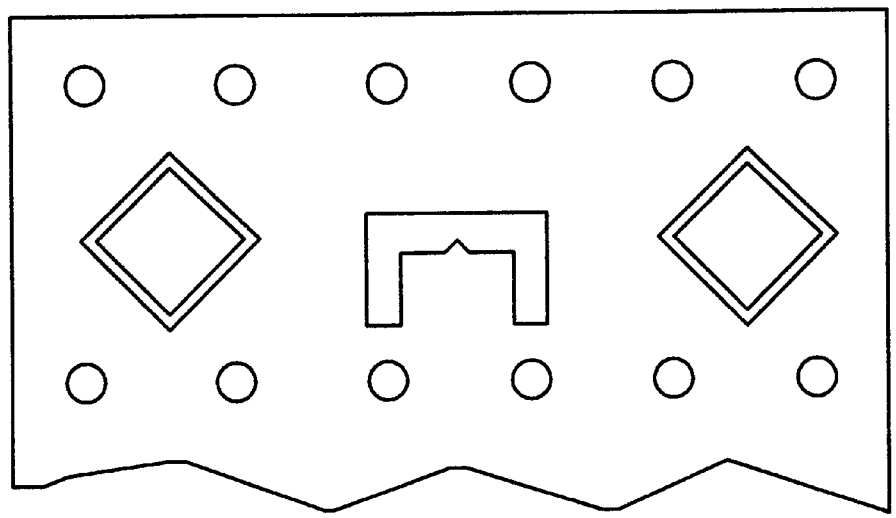
Figure 3I:
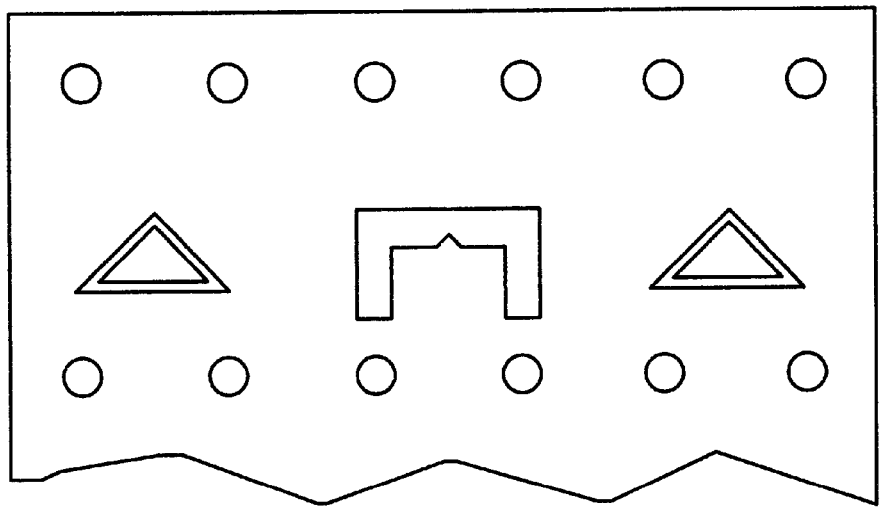
Figure 3J:
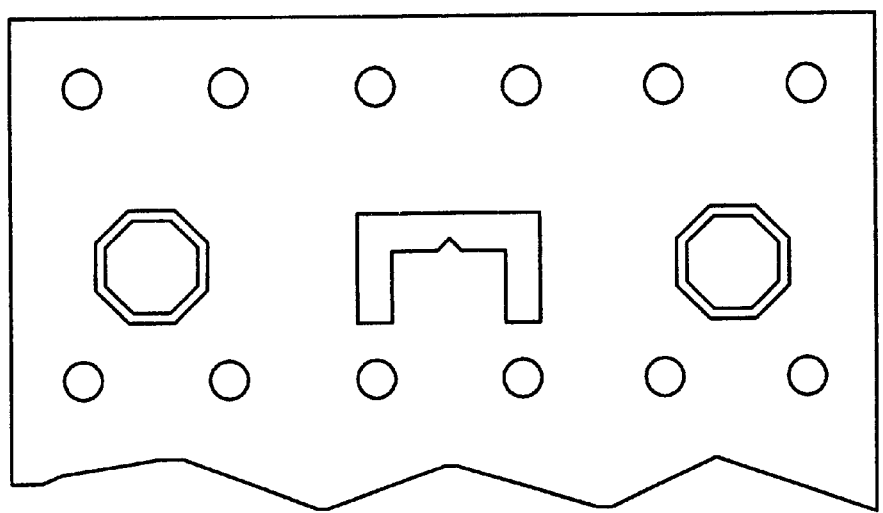
Figure 3K:
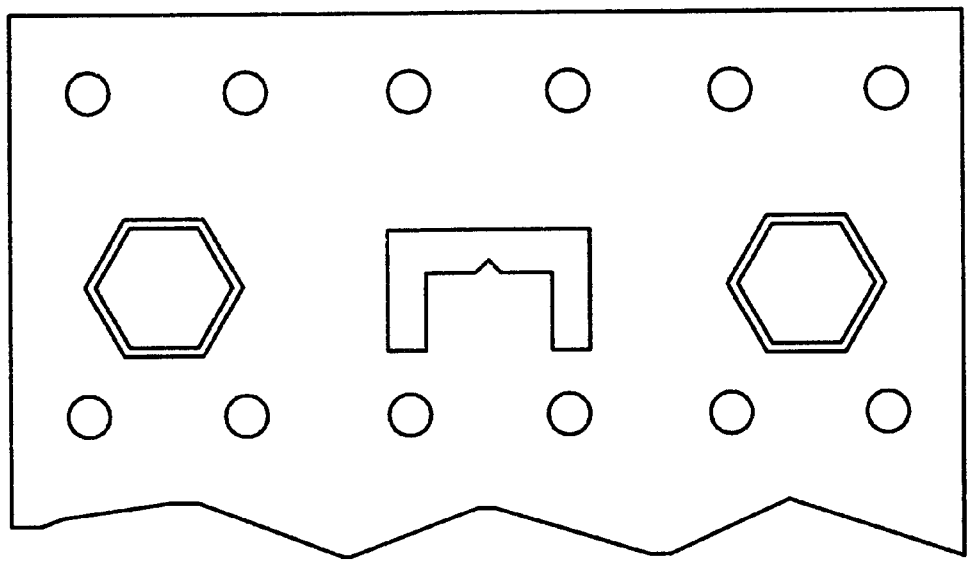
Figure 3L:
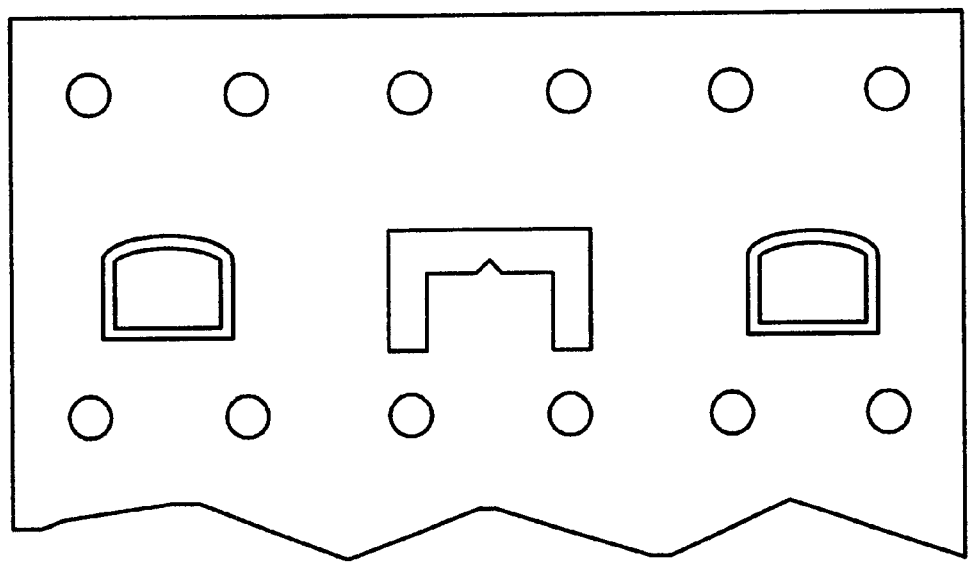
Figure 4:
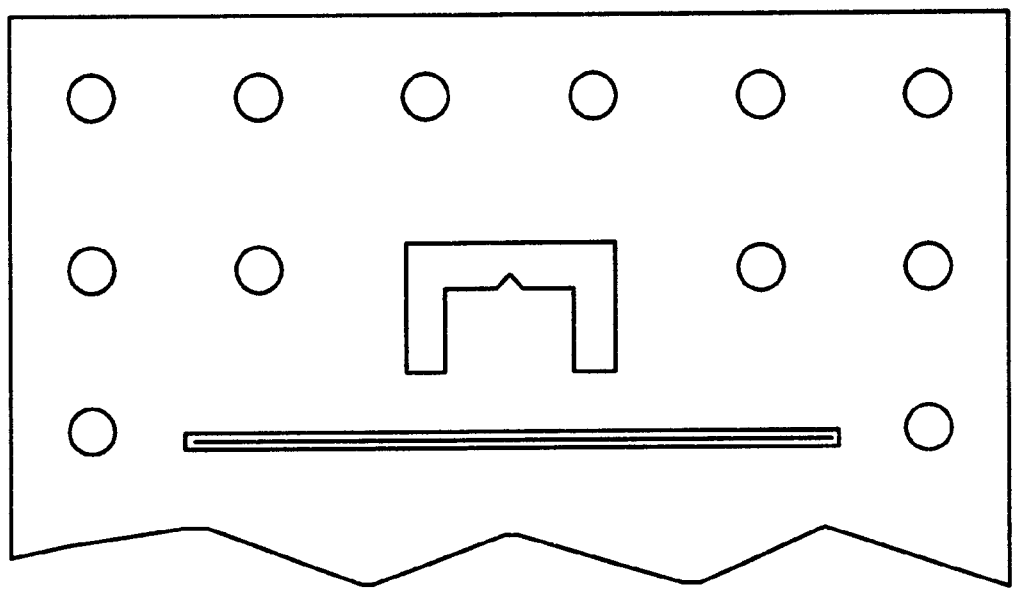
FIG. 4 is a plan view of the lower portion of a blanket according to the present invention showing a single opening.

For example, FIG. 3A shows the lower portion of a blanket according to the present invention having openings formed widthwise across the blanket. FIGS. 3B and 3C show the lower portion of a blanket according to the present invention having openings formed diagonally along the blanket. FIG. 3D shows the lower portion of a blanket according to the present invention having oval openings. FIGS. 3E and 3F show the lower portion of a blanket according to the present invention having oval openings. FIGS. 3G and 3H show the lower portion of a blanket according to the present invention having rectangular openings. FIGS. 3I, 3J, 3K and 3L show the lower portion of a blanket according to the present invention having various geometrically shaped openings.

In addition, while the embodiments shown in the drawing figures show blankets have two openings, it will be recognized that one opening may be utilized, wherein the opening allows both feet of the patient to protrude therethrough.

Figure 2:
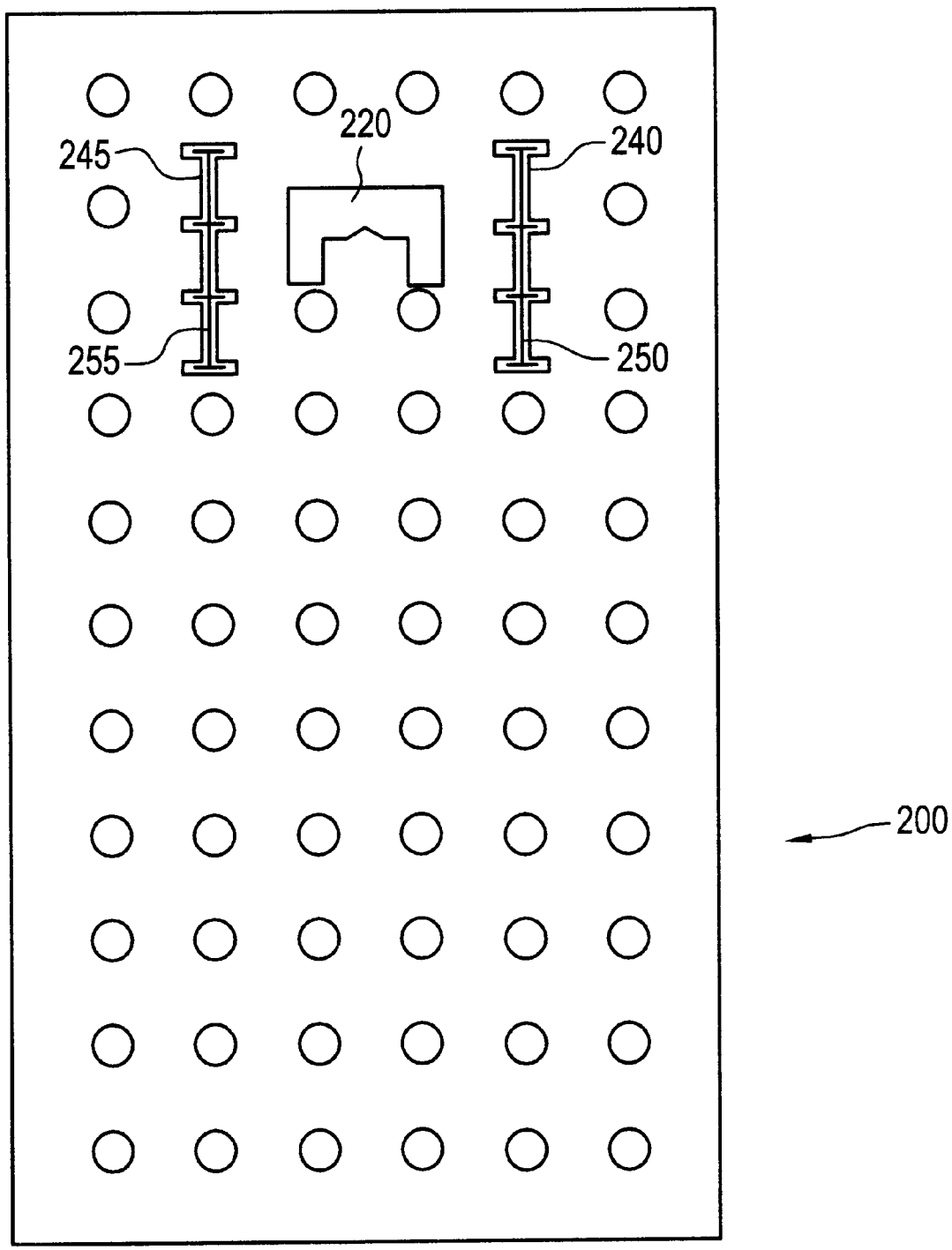
FIG. 2 is a plan view of a blanket according to another embodiment of the present invention.

A further embodiment of the present invention is shown in FIG. 2, wherein a blanket, generally designated be reference numeral 200, has an inlet port 220, and opening 240, 245, in the form of slits having both lengthwise and widthwise components. In this embodiment, the openings 240, 245 are initially closed but include perforations, 250, 255, to allow the openings 240, 245 to be opened. It will be recognized that the openings 240, 245, could be permanently open without the provision of perforations.

The blankets according to the present invention overcomes all of the disadvantages noted above. In particular, when in use, the blankets according to the present invention allow the patient's toes or feet to protrude through the openings. This helps to alleviate the pressure on the toes and feet of the patient and increases the comfort to the patient. In addition, when the toes or feet of the patient protrude through the openings of the blanket, they act as a stabilizer and reduce the amount of slippage. This helps to keep the blanket in place on the patient and to maintain even heating to the patient.

The above embodiments have been described primarily as relating to blankets for use in the PACU. However, it will be recognized that the present invention is equally applicable for blankets to be used in the operating room or other areas of the hospital. In addition, the blankets shown in FIGS. 1 and 2 represent full body blankets but would be equally applicable to blankets intended to cover only the lower body of a patient. Moreover, the blankets above have been primarily discussed as relating to providing warming to a patient, but would be equally applicable for cooling a patient, if so desired. Finally, the blankets according to the present invention would be equally useful in both adult and pediatric sized blankets.

The blanket may be formed of any suitable material capable of being sealed together at selected positions and having sufficient strength to allow inflation and adequate air distribution within the inflated portion. Such materials include plastics, non-woven wood pulp compositions, laminated plastic and wood pulp materials, and combinations thereof.

The foregoing has been a description of certain preferred embodiments of the present invention, but is not intended to limit the invention in any way. Rather, many modifications, variations and changes in details may be made within the scope of the present invention.

What is claimed is:

1. A blanket for use with a forced air convection system comprising:
   a first sheet of material;
   a second sheet of material sealed to said first sheet of material along peripheral edges of said first and second sheets of material to form an inflatable chamber therebetween;
   wherein said blanket includes a first end for positioning toward the head of a patient when said blanket is in use, a foot end for positioning near the feet of a patient when said blanket is in use, and two side edges and connecting said first end and said foot end;
   an inlet port formed in said blanket and communicating with said inflatable chamber; and
   at least two foot openings extending through said first and said second sheets of material, said openings having the two sheets of material sealed around the peripheral edges of the openings, for a patient's toes or feet to protrude through when said blanket is in use, said foot openings located near said inlet port and positioned adjacent to the foot end of said blanket, inwardly from said foot end and said side edges of said blanket, said foot openings located on opposite sides of said inlet port with said inlet port positioned between said foot openings.

2. A blanket according to claim 1, wherein said openings are in the shape of slits which run lengthwise along said blanket.

3. A blanket according to claim 1, wherein said openings are in the shape of slits which run widthwise along said blanket.

4. A blanket according to claim 1, wherein said openings are in the shape of slits which run diagonally along said blanket.

5. A blanket according to claim 1, wherein said openings are in the shape of slits which include first portions running lengthwise along said blanket and second portions running widthwise along said blanket.

6. A blanket according to claim 1, wherein said openings are have a geometric shape selected from the group consisting of circles, ovals, rectangles or polygons.

7. A blanket according to claim 1, wherein said openings are initially closed by means of a perforated section of said blanket.

\* \* \* \* \*